United States Patent [19]

Gruber

[11] Patent Number: 5,030,623

[45] Date of Patent: Jul. 9, 1991

[54] METHODS FOR INCREASING EXTRACELLULAR ADENOSINE AND FOR STABILIZING MAST CELLS

[75] Inventor: Harry E. Gruber, San Diego, Calif.

[73] Assignee: The Regents of the University of California, Oakland, Calif.

[21] Appl. No.: 366,167

[22] Filed: Jun. 14, 1989

Related U.S. Application Data

[60] Division of Ser. No. 79,657, Jul. 29, 1987, Pat. No. 4,912,092, which is a continuation-in-part of Ser. No. 845,627, Mar. 27, 1986, abandoned, which is a continuation-in-part of Ser. No. 646,785, Sep. 4, 1984, abandoned.

[51] Int. Cl.$^5$ .............................................. A61K 31/70
[52] U.S. Cl. ....................................... 514/45; 514/46; 514/826; 514/861; 514/885; 514/886
[58] Field of Search .................. 514/45, 46, 826, 861, 514/885, 886

[56] References Cited

U.S. PATENT DOCUMENTS

| | | | |
|---|---|---|---|
| 4,211,771 | 7/1980 | Witkowski | 514/43 |
| 4,322,806 | 6/1982 | Atsumi | 514/398 |
| 4,432,990 | 2/1984 | Robinson | 514/398 |
| 4,575,498 | 3/1986 | Holmes | 514/43 |

Primary Examiner—John W. Rollins
Attorney, Agent, or Firm—Brown, Martin, Haller & McClain

[57] ABSTRACT

Methods for increasing extracellular concentrations of adenosine for the prophylactic or affirmative treatment of diseases of the immune, nervous, cardiac, and vascular systems involving administering to a patient purine nucleoside and purine nucleoside-related analogs which increase extracellular adenosine concentration, and methods for stabilizing mast cells by the suppression of mast cell activation using such compounds.

16 Claims, 12 Drawing Sheets

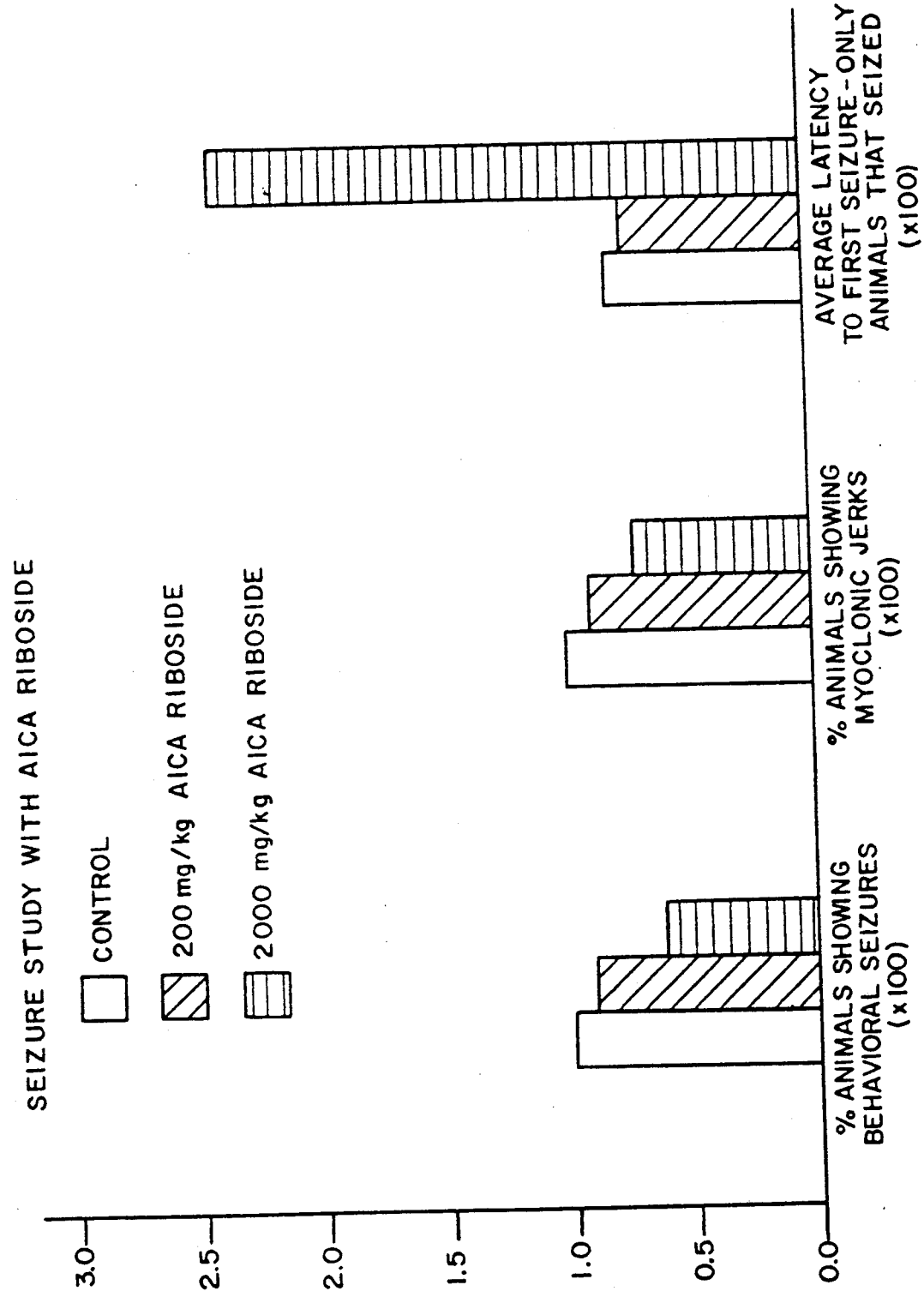

METHODS FOR INCREASING EXTRACELLULAR ADENOSINE AND FOR STABILIZING MAST CELLS

RELATED APPLICATIONS

This is a division of application Ser. No. 07/079,657 now U.S. Pat. No. 4,912,092, filed Jul. 29, 1987, which is a continuation-in-part of Ser. No. 06/845,627 filed Mar. 27, 1986 now abandoned, and which is a continuation-in-part of Ser. No. 06/646,785 filed Sept. 4, 1984 now abandoned.

BACKGROUND OF THE INVENTION

1. Field of the Invention

This invention relates to methods for prophylactically and affirmatively treating various bodily states that respond beneficially to increases in extracellular levels of adenosine by providing patients with purine nucleosides, purine nucleotides, and derivatives, intermediates and analogs thereof. The invention also relates to the stabilization of mast cells with such compounds by suppression of mast cell activation.

2. Description of Related Art

Adenosine, 9-$\beta$-D-ribofuranosyladenine (the nucleoside of the purine adenine), belongs to the class of biochemicals termed purine nucleosides and is a key biochemical cell regulatory molecule, as described by Fox and Kelly in the *Annual Reviews of Biochemistry*, Vol. 47, p. 635, 1978. It interacts with a wide variety of cell types and is responsible for a myriad of biological effects. For instance, adenosine is a potent vasodilator, an inhibitor of immune cell function, and can at certain levels enhance activation of mast cells, is an inhibitor of granulocyte oxygen-free radial production, is antiarrhythmic, and is an inhibitory neutransmitter. Considering its broad spectrum of biological activity, considerable effort has been aimed at establishing practical therapeutic uses for adenosine and its analogs.

Since adenosine is thought to act at the level of the cell plasma membrane by binding to receptors anchored in the membrane, past work has included attempts to increase extracellular levels of adenosine by administration of it into the blood stream. Unfortunately, adenosine is toxic at concentrations that have to be administered to a patient to maintain an efficacious extracellular therapeutic level, and the administration of adenosine alone is therefore of limited therapeutic use. Further, adenosine receptors are subject to negative feedback control following exposure to adenosine, including down-regulation of the receptors.

Other ways of achieving the effect of a high local extracellular level of adenosine exist and have also been studied. They include: (a) interference with the uptake of adenosine with reagents that specifically block adenosine transport, as described by Paterson et al., in the *Annals of the New York Academy of Sciences*, Vol. 255, p. 402 (1975); (b) prevention of the degradation of adenosine, as described by Carson and Seegmiller in *The Journal of Clinical Investigation*, Vol. 57, p. 274 (1976); and (c) the use of analogs of adenosine constructed to bind to adenosine cell plasma membrane receptors.

There are a large repertoire of chemicals that can inhibit the cellular uptake of adenosine. Some do so specifically and are essentially competitive inhibitors of adenosine uptake, and others inhibit nonspecifically. P-Nitrobenzylthioguanosine appears to be a competitive inhibitor, while dipyridamole and a variety of other chemicals, including colchicine, phenethylalcohol and papaverine inhibit uptake nonspecifically.

Extracellular levels of adenosine can be increased by the use of chemicals that inhibit enzymatic degradation of adenosine. Previous work has focused on identifying inhibitors of adenosine deaminase, which participates in the conversion of adenosine to inosine. Adenosine deaminase activity is inhibited by coformycin, 2'-deoxycoformycin, and erythro 9-(2-hydroxy-3-nonyl) adenine hydrochloride.

A number of adenosine receptor agonists and antagonists have been generated having structural modifications in the purine ring, alterations in substituent groups attached to the purine ring, and modifications or alterations in the site of attachment of the carbohydrate moiety. Halogenated adenosine derivatives appear to have been the most promising as agonist or antagonist and, as described by Wolff et al. in the *Journal of Biological Chemistry*, Vol. 252, p. 681, 1977, exert biological effects in experimental systems similar to those caused by adenosine.

Although all three techniques discussed above may have advantages over the use of adenosine alone, they have several disadvantages, the major disadvantages being that they rely on chemicals that have adverse therapeutic side effects, primarily due to the fact that they must be administered in doses that are toxic, and that they affect nonselectively most cell types. As described in *Purine Metabolism in Man*, (eds. De Baryn, Simmonds and Muller), Plenum Press, New York, 1984, most cells in the body carry receptors for adenosine. Consequently, the use of techniques that increase adenosine levels generally throughout the body can cause unwanted, dramatic changes in normal cellular physiology.

With respect to post ischemic myocardial tissue and adenosine, it is stated in Swain, J. L., J. J. Hines, R. L. Sabina, and E. W. Holmes, *Circulation Research* 51: 102–105 (1982), and in Holmes et al., U.S. Pat. No. 4,575,498 (issued Mar. 11, 1986), that adenosine concentration and blood flow are not altered in ischemic canine hearts exposed to the purine nucleoside 5-amino-4-imidazolecarboxamide riboside (AICA riboside). They also state that depletion of purine nucleotide pools, especially adenosine triphosphate (ATP), has been postulated to play a role in such dysfunction following, e.g., an ischemic event, and claim to have demonstrated an enhanced nucleotide synthesis and concomitant repletion of ATP pools by treating post-ischemic myocardium with the purine analog AICA riboside, stating that repletion of ATP pools should, in theory, enable the amelioration of tissue damage.

Several other groups of investigators, however have published studies in which they were unable to demonstrate an enhanced repletion of ATP pools in ischemic tissue by the method of Swain et al., supra. Mentzer, R. M., Ely, S. W., Lasley, R. D., Lee, B. K. and Berne, R. M., *Fed. Proc.* 43: 903 (1984); Mitsos, S. E., S. R. Jolly and B. R. Lucchesi, *Pharmacology* 31: 121–131 (1985); Hoffmeister, H. M., Nienaber, C., Mauser, M. and Schaper, W. E., *Basic Research in Cardiology* 80: 445–458 (1985); Mauser, M., H. M. Hoffmeister, C. Nienaber, and W. E. Schaper, *Circul. Res.* 56: 220–230 (1985). In fact, Hoffmeister et al. demonstrate that ATP repletion by another mechanism does not improve cardiac dysfunction. Even Holmes and Swain have documented that AICA riboside does not effectively reach ATP because of an inhibition of the conversion of inosine monophosphate (IMP) to adenosine monophosphate (AMP). Sabina, R. L., Kernstine, K. H., Boyd, R. L., Holmes, E. W. and Swain, J. L., *J. Biol. Chem.* 257: 10178 (1982); Amidon, T. M., Brazzamano, S., Swain, J. L., *Circ. Suppl.* 72: 357 (1985); Swain, J. L., Hines, J. J., Sabina, R. L., Harburg, O. L. and Holmes, E. W., *J. Clin. Invest.* 74: 1422–1427 (1984). Amidon et al., supra, state that "These results indicate that adenylosuccinate synthetase and/or lyase activities are limiting in isolated hearts and suggest that interventions designed to bypass IMP in AN (Adenine Nucleotide) synthesis might be more advantageous for increasing AN pool size." Swain et al., supra (*J. Biol. Chem.*), also demonstrated that AICA riboside does not alter ATP levels in non-ischemic myocardium.

While Mitsos et al., supra, claimed that their study demonstrated that AICA riboside infused intracoronary in high doses protected globally ischemic hearts from the mechanical dysfunction associated with an ischemic insult, Hoffmeister et al., *Basic Res. Cardiol.* 80: 445–458 (1985), showed that on producing a reversible ischemia in dogs by coronary artery occlusion, AICA riboside application did not improve postischemic function and, in fact, worsened it. Swain et al., supra (*J. Clin. Invest.*) confirms the detrimental effects of high doses of AICA riboside on muscle contractility. Thus, the proposal that the administration of AICA riboside would be of benefit to patients after an ischemic event for repletion of ATP pools does not appear to be valid.

It will be appreciated from the foregoing discussion that a technique that would increase extracellular levels of adenosine or adenosine analogs at specific times during a pathologic event, that would increase these compounds without complex side effects, and which would permit increased adenosine levels to be selectively targeted to cells that would benefit most from them would be of considerable therapeutic use. By way of example, such a technique would be especially useful in the prevention of, or response during, an ischemic event, such as heart attack or stroke, or other event involving an undesired, restricted or decreased blood flow, such as atherosclerosis, for adenosine is a vasodilator and prevents the production of superoxide radicals. Such a technique would also be useful in the prophylactic or affirmative treatment of pathologic states involving increased cellular excitation, such as (1) seizures or epilepsy, (2) arrhythmias, and (3) inflammation due to, for example, arthritis, autoimmune disease, Adult Respiratory Distress Syndrome (ARDS), and granulocyte activation by complement from blood contact with artificial membranes as occurs during dialysis or with heart-lung machines. It would further be useful in the treatment of patients who might have chronic low adenosine such as those suffering from autism, cerebral palsy, insomnia and other neuropsychiatric symptoms, including schizophrenia. The compounds useful in the invention, which include AICA riboside, may be used to accomplish these ends.

Another area of medical importance is the treatment of allergic diseases, which can be accomplished by either preventing mast cells from activating, or by interfering with the mediators of allergic responses which are secreted by mast cells. Mast cell activation can be down-regulated by immunotherapy (allergy shots) or by mast cell stabilizers such as cromalyn sodium, corticosteroids and aminophylline. There are also therapeutic agents which interfere with the products of mast cells such as anti-histamines and adrenergic agents. The mechanism of action of mast cell stabilization is not clearly understood. In the case of aminophylline, it is possible that it acts as an adenosine receptor antagonist. However, agents such as cromalyn sodium and the corticosteroids are not as well understood.

It will be appreciated, therefore, that effective allergy treatment with compounds which will not show any of the side effects of the above-noted compounds, such as drowsiness in the case of the anti-histamines, agitation in the case of adrenergic agents, and Cushing disease symptoms in the case of the corticosteroids, would be of great significance and utility. In contrast to compounds useful in the invention, such as AICA riboside and ribavirin, none of the three known mast cell stabilizers are known or believed to be metabolized in the cell to purine nucleoside triphosphates or purine nucleoside monophosphates.

SUMMARY OF THE INVENTION

Novel methods are described for enhancing adenosine release, especially during net ATP catabolism, i.e., during a time of a decreasing or decreased ratio of ATP synthesis to ATP breakdown in cells or cellular compartments.

Novel methods are also described for stabilizing mast cells.

Also included within the scope of the invention is a method of screening purine nucleoside compounds or analogs for the ability to enhance the cellular synthesis and release of adenosine comprising administering to cultured cells a first composition comprising a purine nucleoside compound or analog to be screened, administering to said cultured cells a second composition comprising a compound which promotes net catabolism of adenosine triphosphate, and determining the level or amount of adenosine released by said cultured cells.

This last method may further comprise a first control set of cultured cells to which neither said first composition nor said second composition is added, a second control set of cultured cells to which said first composition is added, and a third control set of cultured cells to which said second composition is added. The cultured cells may be derived from a human malignant cell line, such as Epstein-Barr virus transformed B lymphocytes, or the WI-L2 human splenic lymphoblast cell line, such as that used in Example II herein. Compounds used to create compositions for the promotion of net catabolism of adenosine triphosphate include calcium ionophores and 2-deoxyglucose.

Methods for enhancing adenosine release utilize the administration of compounds which are believed to alter one or more of the biochemical pathways of adenosine metabolism so that the net result is an enhanced extracellular concentration of adenosine (resulting from one or more processes, including enhanced intracellular production and/or release of adenosine). Examples of compounds useful in the invention include compounds broadly classified as purine nucleosides and related analogs, such as AICA riboside, AICA ribotide, 1-$\beta$-D-ribofuranosyl-1H-1,2,4-triazole-3-carboxamide (ribavirin), ribavirin monophosphate, and various pro-forms of the above compounds. The compounds are taken up by cells and, if necessary, are believed to be converted to their monophosphate and, to a lesser extent, their triphosphate forms. Also included are (1) agents that can enhance endogenous synthesis of AICA ribotide or metabolites, such as purine intermediary metabolites or compounds that can form these metabolites, e.g., succinylaminoimidazole carboxamide (SAICA) riboside, (2) agents that cause a buildup of AICA-ribotide or its metabolites, including methotrexate, and (3) agents that cause bacterial flora to increase AICA riboside production, such as sulfonamides. These compounds can be administered to a patient either prophylactically, in some cases, and/or in direct response to a bodily condition in others. Purine nucleosides that enhance the excretion of cellular adenosine and/or adenosine analogs may be administered to a living system over the concentration range of 0.5 molar to 0.5 molar and, typically, are administered in concentrations up to 0.5 molar.

Adenosine or inosine are generated from adenosine triphosphate in the course of rapid cellular energy utilization, such as during seizure activity, arrhythmias, or a condition resulting in decreased blood flow (ischemia), such as a stroke, heart attack, or angina. Normally, during such an event, the production of inosine is greater than that of adenosine. In the area of low flow during coronary occulusion, for example, the ratio of inosine to adenosine is approximately 100 to 1. A certain percentage of inosine and adenosine subsequently exit the cell and are present in the immediate extracellular environment. The compounds useful in the methods described and claimed herein have been shown to enhance the extracellular concentration of adenosine, and the production of inosine has been shown to be decreased. Adenosine levels are not altered significantly throughout the patient because alterations in adenosine production only occur in areas of, and at the time of, net ATP use and because adenosine is rapidly degraded. Thus, the methods described and claimed herein will cause a localized increased concentration of extracellular adenosine instead of a systemic or generalized adenosine enhancement.

Oxidation of low density lipoprotein (LDL) is one of the first, if not the first, steps in the process of atherosclerosis, a process believed to involve inflammation and to be due to mononuclear cell and/or granulocyte activation. The oxidized lipids are taken up by macrophages to form the atherosclerotic plaque. Because adenosine prevents the production of superoxide radicals, the compounds of the invention which enhance adenosine release should slow, prevent, or reverse the development of atherosclerosis.

Patients that are suffering from (1) autoimmune disease, (2) arthritis, (3) psoriasis, (4) organ transplant rejection, (5) complement-mediated granulocyte activation after exposure to heart-lung or dialysis membranes, (6) ARDS, or other inflammatory conditions, whether due to granulocyte activation (as (1)–(6) above can be) or mononuclear cell activation, should also experience relief on treatment with the compounds useful in the invention because ATP catabolism is expected during an inflammatory response.

Patients suffering from diseases which may be associated with chronic low adenosine, such as insomnia, autism, schizophrenia and cerebral palsy, will also benefit from the use of the invention to increase adenosine concentrations.

Further, treatment with compounds of the invention will benefit patients suffering from a variety of illnesses relating to mast cell degranulation. They include individuals suffering from allergies, particularly asthma, hay fever, chronic urticaria, urticaria pigmentosa and eczema. Both AICA riboside and ribavirin, for example, suppress mast cell activation, including the prevention of mast cell degranulation. Decreased mast cell activity will also benefit patients with reduced blood flow because agents released from mast cells can increase damage during ischemia through processes such as arrhythmias or vessel spasm.

It is anticipated that compounds useful in the invention will be effectively administered in amounts ranging from about 0.1 mg/kg/day to about 500 mg/kg/day, preferably from about 15 mg/kg/day to about 200 mg/kg/day. That range of dosages should be especially suitable for compounds useful in the invention as prophylactics for the prevention of tissue damage associated with undesired restricted or decreased blood flow. The use of at least about 0.1 mg/kg/day of AICA riboside or AICA ribotide, preferably from about 1.0 mg/kg/day to about 500 mg/kg/day for said prophylaxis and, more preferably, from about 20 mg/kg/day to about 100 mg/kg/day, is further anticipated. Also contemplated for said prophylaxis is the administration of ribavirin or ribavirin monophosphate in an amount of at least about 0.1 mg/kg/day, preferably from about 1.0 mg/kg/day to about 20 mg/kg/day. In the case of treatment of brain diseases, such as stroke, seizures, epilepsy, transient ischemic attack, autism, schizophrenia, cerebral palsy and insomnia, a dosage of more than 200–500 mg/kg/day may be needed because of the blood/brain barrier. The use of brain-directed pro-drugs may, however, enable a lower dosage.

BRIEF DESCRIPTION OF THE DRAWINGS

FIG. 12. AICA riboside inhibition of pentylene tetrazol-induced seizures in the rat.

DETAILED DESCRIPTION OF THE INVENTION

Figure 1:
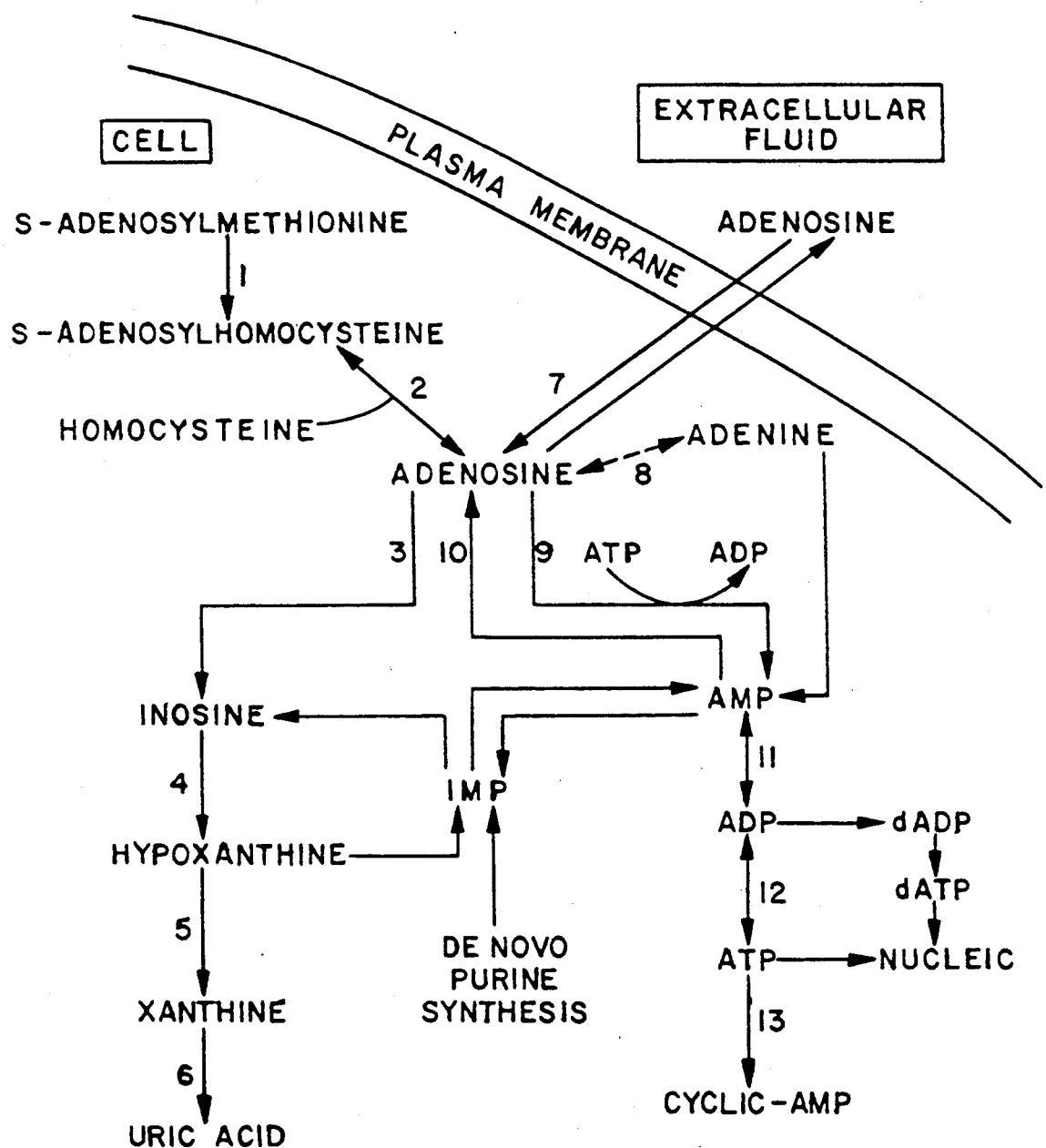
FIG. 1. Metabolic pathways of adenosine.

FIG. 1 illustrates the pathways by which adenosine is formed and degraded within cells. Adenosine may be transported into cells or released from cells. The metabolism of adenosine may utilize some of these pathways: 1, S-adenosylmethionine methyltransferase; 2, S-adenosylhomocysteine hydrolase; 3, adenosine deaminase; 4, purine nucleoside phosphorylase; 5 and 6, xanthine oxidase; 7, transport mechanisms; 8, adenosine phosphorylase (not established in humans); 9, adenosine kinase; 10, 5' nucleotidase and nonspecific phosphatase; 11, adenylate kinase; 12, nucleoside diphosphokinase; 13, adenylate cyclase; 14, AMP deaminase; and 15, adenylosuccinate synthetase and adenylosuccinate lyase.

As described in more detail below, the effects of the use of the compounds described, including the purine nucleosides ribavirin and AICA riboside, on extracellular adenosine concentration have been demonstrated both in vitro and in vivo. To deliver these molecules to patients, it is anticipated that they will most often be administered orally, since the compounds of the invention are not readily degraded by extracellular enzymes in the body or by exposure to low pH present in the stomach. These drugs can also be administered intravenously, by direct intramuscular injection, subcutaneously, topically to skin or mucous membranes, rectally, or by inhalation. Compositions acceptable for pharmaceutical use are well known. Pro-drugs may also be utilized, i.e., those which, when introduced into the body, metabolize to the active forms of the claimed compounds.

Because the purine nucleoside AICA riboside can be metabolized to uric acid, this agent may be used with allopurinol or other drugs that prevent uric acid synthesis, or with a uricosuric agent such as probenicid. Certain agents, such as methotrexate and ribavirin, whose metabolites inhibit AICA ribotide transformylase, may cause an elevation of endogenously synthesized AICA ribotide and create effects similar to administering the purine nucleoside. Concomitant administration of AICA riboside or AICA ribotide with an inhibitor of AICA ribotide transformylase should have at least additive effects. In addition, any one of the de novo purine nucleotide synthesis intermediates (after the first committed step for purine synthesis) or their nucleosides or bases can be assumed to be rapidly converted to AICA ribotide. An example is SAICA ribotide or its nucleoside or base.

The compounds can be used to enhance extracellular concentrations of adenosine and, therefore, to treat diseases that arise from, or are aggravated by, insufficient blood flow through a particular organ or portion thereof. For example, heart attacks or strokes, the microvascular disease of diabetes mellitus (which can affect the brain, the kidney, the heart, the skin, the retina, and the peripheral nerves and their associated microvasculatures), or events resulting in a less prolonged loss of blood flow, such as angina pectoris, transient ischemic attacks, bowel ischemia, kidney ischemia, intermittant claudication of skeletal muscle, migraine headaches, and Raynaud's phenomenon can be treated by administering the compounds of the invention. Adenosine is known to be both a potent vasodilator, which acts by reducing vascular smooth muscle contraction, and an inhibitor of granulocyte free radical production, a process involved in ischemic injury. As noted, it should also be useful in the treatment of atherosclerosis.

Upon contact with cells, it is believed that the compounds useful in the invention enter the cell where they can be phosphorylated by adenosine kinase or, in the case of administration of base, they can be converted to a nucleotide by a phosphoribosyl transferase enzyme to yield a purine nucleotide monophosphate, and eventually also the nucleoside triphosphate. The triphosphate form may comprise a pool for breakdown to the monophosphate form.

While not wishing to be bound by the following proposed mode of action, it is postulated that the compounds of the invention, or their metabolites, inhibit one or more enzymes in the adenosine biologic pathway, including AMP deaminase, thus shunting ATP more toward the cellular production, release, and less reuptake of adenosine, and shunting it away from, concomitantly, the cellular production and release of inosine.

It is important to note that ribavirin cannot be metabolized into normal purines, i.e., it does not become AMP, ADP, ATP, IMP, or the guanosine phosphates GMP, GDP, or GTP. In other words, the compounds useful in the invention can enhance adenosine release without being directly metabolized into adenosine. AICA riboside has biochemical properties similar to ribavirin and appears to enhance adenosine release by a similar mechanism rather than by a circuitous conversion to adenosine. The compounds have been shown not to act by the repletion of ATP pools.

FIG. 1 shows that adenosine is primarily metabolized in either of two ways. First, as shown by pathway 3, adenosine may be catabolized by the enzyme adenosine deaminase to form inosine. Inosine is then, for the most part, either further degraded by the enzymes represented in pathways 4, 5 and 6, or shunted out of the cell across the plasma membrane. Transport mechanisms 7 are shown, which enable the transport of adenosine across the cellular plasma membrane in both directions.

Adenosine may also be anabolized by the enzyme adenosine kinase, represented by 9, to adenosine monophosphate (AMP) or to S-adenosylhomocysteine by S-adenosylhomocysteine hydrolase, represented by 2 (depending on homocysteine availability). The former is an energy-requiring reaction. AMP is then either acted on by the enzyme AMP deaminase (14) to form inosine monophosphate (IMP), or further anabolized by various enzymatic reactions to form adenosine triphosphate (ATP) or cyclic-AMP. Inhibition of adenosine kinase or S-adenosylhomocysteine hydrolase can indirectly lead to a decrease in uptake of adenosine.

Referring to Examples I-III on the release of adenosine, it is shown by the results in FIGS. 2, 3, 7-9, and Table I, that the presence of AICA riboside during ATP catabolism increases cellular release of adenosine and, concomitantly, decreases cellular release of inosine (see Example IV and FIG. 5), suggesting that there is an inhibition of the conversion of AMP to IMP, or that there is an inhibition of the conversion of adenosine to inosine.

Figure 6:
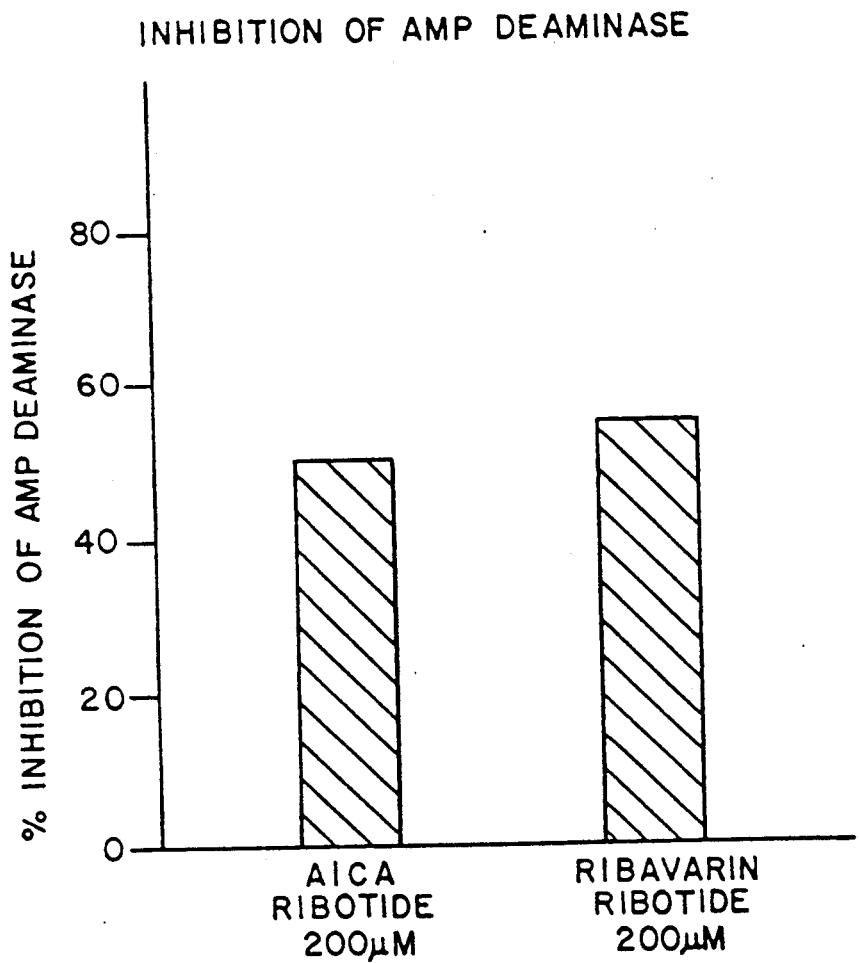
FIG. 6. Effects of AICA ribotide and ribavirin ribotide on inhibition of the enzyme AMP deaminase.

The cell culture experiments of Examples I and II show that AICA riboside increases the cellular release of adenosine even in the presence of 2-deoxycoformycin, a potent inhibitor of the enzyme adenosine deaminase. Thus, it appears that the compounds of the invention have their effect at a point in the adenosine pathway other than or in addition to the reaction catalyzed by adenosine deaminase. They are believed to inhibit the conversion of AMP to IMP by interfering with the action of the enzyme AMP deaminase. The ability of metabolites of the compounds of the invention to inhibit the enzyme AMP deaminase was evaluated in Example VII, and the results are shown in FIG. 6. AICA ribotide and a structurally similar compound, ribavirin monophosphate, were shown to have similar inhibitory effects on AMP deaminase.

It is also possible, however, that the compounds of the invention inhibit the enzymatic conversion of IMP to inosine by 5' nucleotidase, thus decreasing the breakdown of IMP, the result being an increase in the amount of cellular release of adenosine. Further, the compounds of the invention may act to inhibit, directly or indirectly, cellular re-uptake, phosphorylation, or deamination of adenosine.

In summary, a suggested pathway enabling the beneficial effect seen with compounds useful in the invention is the entry of such compounds into the cell, where they become ribosylated (if the sugar ring is not yet present) and phosphorylated (if not yet phosphorylated) to their monophosphate form. The monophosphate forms of the claimed compounds inhibit AMP deaminase. During ATP catabolism, the AMP pool increases more in treated cells than in untreated cells because AMP is no longer able to move as readily to IMP. Cleavage of the purine monophosphates results in a higher cellular release of adenosine with a concomitant lower cellular release of inosine. Because adenosine appears to be a natural beneficial mediator during certain pathological events, enhancement of its release by channeling ATP to adenosine instead of inosine is a novel and extremely important method of treatment.

During a heart attack, adenosine is normally released and it assists in maintaining the patency of ischemic vessels through vasodilation and inhibition of granulocyte free radical production and concomitant microvascular plugging, as described below. The compounds useful in the invention enhance adenosine release and, therefore, enhance the normal protective effect of adenosine during such an ischemic event.

While the release of adenosine is at times a beneficial event, high levels of adenosine in areas where it is not required can be detrimental. One virture of the invention described and claimed herein is that the patient is not treated with adenosine itself and the compounds useful in the invention selectively increase adenosine release from cells in which there is a net ATP breakdown. Thus, only cells in the vicinity are treated. Treatment of patients with compounds useful in the invention allows the targeting of enhanced adenosine release specifically to tissue undergoing net ATP catabolism, i.e., to tissue which is in need of adenosine release. The systemic effects of adenosine administration are avoided. Further, adenosine is released only at the specific time it is needed. All diseases and pathologic states described or disclosed herein involve or are believed to involve localized net ATP catabolism.

Additionally, cells that would respond beneficially to adenosine are more responsive than they would be if they were continually bathed in higher concentrations of adenosine. Because adenosine is available only instantaneously when it is needed, receptors on the surfaces of cells, such as granulocytes and smooth muscle cells, are not continually exposed and, therefore, have a much larger response, as their adenosine receptors have not been downregulated by continual adenosine exposure.

In addition to acting to cause vasodilation through the release of adenosine, the compounds of the invention can increase collateral blood flow by a second mechanism. Studies have shown that in the region of restricted blood flow, granulocytes become activated, release oxygen-free radicals, and subsequently stick in and damage microvasculature. Drugs useful in the invention through enhanced adenosine release prevent granulocytes from producing the free radicals and, therefore, granulocytes stick less in the microvessels (see Example VIII), which allows blood flow from collateral vessels into the blocked area. As shown by Example IX, indium-labelled granulocytes are washed out of AICA riboside-treated dog hearts at one hour of ischemia significantly more than in saline-treated dogs, leading to increased collateral blood flow. Thus, the uptake of the compounds of the invention by muscle and/or endothelial cells, followed by subsequent release of adenosine during ischemia, should cause vasodilation and/or suppression of granulocyte activation and inhibit concomitant clogging and damage of the microvasculature, thereby leading to a reduction in damage to the cardiac muscle.

As shown by Examples I-VI, IX, XIII, and XIV, an important aspect of the compounds of the invention is that they can be administered as prophylactic agents. When the drug is present in advance of an ischemic event, seizure activity, or other bodily state targeted for treatment, the net breakdown of ATP can be directed in larger measure to adenosine rather than inosine.

If the drug is introduced into a patient to reach an ischemic region after or during an event causing that ischemia, there is little or no ability to direct ATP to adenosine at that site because the target ATP pools are depleted relatively quickly. Also, because many of the damaging events during ischemia occur rapidly, the drug should ideally be present at the earliest possible moment. With the drug present as a prophylactic agent, there is also the possibility that the process sought to be interrupted can be slowed early enough to prevent any permanent damage. For example, the increased microvascular blood flow from vasodilation and decreased white cell sticking could maintain microvascular patency, as well as in a sense help wash away clots, clot-promoting material, or other deleterious agents from the proximal atherosclerotic regions.

Other factors make it important to administer the drug before or during an ischemic event. If a drug is administered after a blockage, it is less able to reach the tissue involved because there is little or no blood flow to this area. See Example III and FIG. 4. It is also believed that, for example, AICA riboside is metabolized to AICA ribotide and that this is the active form of the molecule. This is an energy-requiring reaction utilizing ATP. If ATP is not available because of high metabolic activity and/or increased ATP destruction, then the AICA riboside or a similar drug cannot be made into its active form. In addition, during rapid ATP breakdown, the inosine in the cell may be significantly competing with the drug for entry into the cell, both compounds being purine nucleoside analogs.

Further, compounds of the invention are envisioned to be beneficial in combination with certain other treatment modalities, as described below. As compounds of the invention, when taken prophylactically, enhance adenosine release during an acute ischemic event, a heart-attack patient undergoing such treatment would have a greater chance of not dying of a sudden arrhythmia before entry to a hospital. In addition, the microvascular bed would be protected during the time the patient is in transit to the hospital and before additional therapy can be instituted.

Often, an acute ischemic event is silent for some time, and there is an additional delay before the patient realizes what is happening and help is sought. When medical help reaches the patient, of course, as when an ambulance arrives or when the patient reaches a hospital, the patient can be given thrombolytic therapy. Thrombolytic therapy, such as the infusion of tissue plasminogen activator (t-PA), streptokinase, urokinase, or anticoagulants such as heparin or Coumadin, are all aimed at opening up a proximal occulsion, such as occurs during a heart attack or stroke. Currently, the patient needs to receive this treatment within about four hours of an acute ischemic event. After several hours, there is irreversible damage to the tissues, especially the microvascular bed. If the patient is prophylactically taking AICA riboside or another compound of the invention, the patient's microvascular bed will be protected longer because of the presence of enhanced adenosine.

The enhanced adenosine release prevents superoxide free radical production and/or granulocyte plugging and damage to the microvessels. Therefore, the patient should be protected for a longer period of time after the acute ischemic event. For example, for perhaps 8–16 hours after a cardiovascular occlusion, it would still be possible to institute one of these thrombolytic therapies in order to open a proximal lesion. Again, opening a proximal lesion is only beneficial if the downstream microvessels are able to be perfused.

Compounds useful in the invention will also be beneficial in combination with thrombolytic agents, such as tissue plasminogen activator, as well as with other agents which are either free radical scavengers or prevent the production of free radicals. Examples of free radical scavengers are superoxide dismutase, a protein which is infused after an ischemic event, or materials which have less proven efficacy, such as catalase, acetyl cysteine (mucomyst), vitamin E, gluthathione, and selenium. Examples of compounds which are thought to prevent free radical production are allopurinol by its inhibition of xanthine oxidase, and icosopentanoic acid by its down regulation of prostaglandin metabolites and, finally, antibodies against certain receptors on activated granulocytes which prevent their sticking in microvessels. Compounds useful in the invention, through elevated adenosine, inhibit the NADPH oxidase free radical-generating system of granulocytes and should, therefore, also be useful when combined with agents such as allopurinol, which inhibits free radical production from xanthine oxidase.

Another disease caused by or able to cause restricted blood flow is myocardial arrhythmia. Although restricted blood flow can initiate the onset of arrhythmia, the precise cause is unknown. However, it is known that lipid peroxidation by oxygen radicals is arrhythmogenic. Since the latter are produced granulocytes, the inhibition of granulocyte superoxide production by the method of the invention can be expected to control arrhythmia. In addition, mast cells are in higher concentration in areas of atherosclerosis. Suppression of their activation might reduce the release of other mediators of arrhythmias. Adenosine also has direct anti-arrhythmic effects on myocytes. The prophylactic effect of AICA riboside treatment on arrhythmias was demonstrated by Examples VI and XIV, the results showing a decreased number of premature ventricular depolarizations and ventricular tachycardia episodes. Rapid firing of cells during arrhythmia causes increased net ATP catabolism and adenosine release.

The adenosine released from neuronal cells when they are stimulated and break down ATP during seizure (epileptic) activity normally will feedback and suppress this seizure (epileptic) activity. In the presence of compounds useful in the invention, the amount of suppression of a seizure event should be significantly increased. Example XIII demonstrates that AICA riboside causes a decreased incidence and prolonged latency to pentylene tetrazol-induced seizures.

Patients that are suffering from autoimmune diseases, arthritis, or other inflammatory conditions should also experience relief if treated with purine nucleosides or analogs useful in the invention because ATP catabolism is expected during the increased cellular excitation associated with an inflammatory response. Inflammatory diseases occur naturally in man and appear to involve an immune reaction to an individual's own tissues. For an autoimmune response to be mounted, it is required that different immune cells interact to support the response. Thus, chemicals that interfere with the requisite cell-cell interactions can be expected to interfere with the course of the disease. One immune cell type necessary for the generation of an autoimmune response is the lymphocyte. Because adenosine is well known to be suppressive to lymphocytes, administering compounds useful in the invention, such as AICA riboside or ribavirin, should inhibit or deplete this population of immune cells during an inflammatory episode, and thus be of considerable therapeutic benefit to inflammatory disease sufferers. Also, as noted, adenosine inhibits granulocyte production of oxygen-free radicals and adherence to endothelial cells, both of which appear to be important factors in many inflammatory processes, such as autoimmune diseases.

Conditions potentially associated with chronic low adenosine may also be treated by compounds of the invention. These pathologic states include autism, insomnia, cerebral palsy, schizophrenia, and other neuropsychiatric symptoms. It is anticipated that doses ranging from 0.1 mg/kg/day up to about 200 mg/kg/day will be beneficial. The results of therapeutic trials with AICA riboside in patients with adenylosuccinase deficiency (autism) are shown in Example X. The oral administration of AICA riboside at a single dose of 5 mg/kg/day, increased to 2×5 mg/kg/day and, finally, to 2×10 mg/kg/day, showed a clear-cut improvement in one of two patients, both patients being described as "more pleasantly active and more easy to handle during therapy" by the father, thereby prompting his request for resumption of the trial. No clinical or biochemical side effects were observed, which suggests that higher doses may be administered with additional beneficial effects.

With respect to mast cell degranulation, treatment with, for example, AICA riboside or ribavirin will benefit patients suffering from a variety of illnesses. For example, individuals suffering from allergies, particularly asthma, hay fever (including allergic conjunctivitis and allergic rhinitis), chronic urticaria, urticaria pigmentosa and eczema, can be expected to benefit from purine nucleoside and purine nucleoside analog treatment. As discussed in B. Benacerra and A. Unanue in *Textbook of Immunology* (Williams & Williams Baltimore/London, 1979), a key to suppressing allergic responses is to prevent the release of pharmacologically active substances by mast cells. Mast cells are large basophilic staining cells with extensive granules that contain substances, such as histamines, that are liberated by the mast cell during an allergic reaction and are required to support the allergic response. The release of these pharmacologically active substances present in mast cells is termed "degranulation." Thus, chemicals that prevent degranulation should have a beneficial effect on reducing the severity of the allergic response. As such, patients experiencing allergies can be successfully treated with AICA riboside or ribavirin, as these molecules prevent mast cell degranulation. Mast cell activation also causes the release of prostaglandins and leukotrienses (non-preformed mediators) such as slow reactive substance of anaphylaxis. The purine nucleosides and analogs useful in the invention also prevent release of these mediators of inflammation. As shown by Example XI, prophylactic treatment of mast cells with ribavirin exhibited a marked attenuation of $\beta$-hexosaminidase release, the results being set forth in FIGS. 10 and 11. The results from Example XII, similarly, showed that AICA riboside inhibits activation (leukotriene $C_4$ release) and degranulation ($\beta$-hexosaminidase release) of mast cells.

To assist in understanding the invention, the results of a series of experiments follow. The following Examples relating to the present invention should not, of course, be construed as specifically limiting the invention, and such variations of the invention, now known or later developed, which would be within the purview of one skilled in this art are to be considered to fall within the scope of this invention as hereinafter claimed.

EXAMPLE I

AICA riboside enhancement of adenosine release by lymphoblasts

With regard to the enhanced in vitro release of adenosine by the claimed method, a human splenic lymphoblast cell line (WI-L2) was used to demonstrate the effect of AICA riboside on adenosine release. The history and properties of the cell line have been described by Hershfield et al. in *Science*, Vol. 197, p. 1284, 1977. The cell line was maintained in RPMI 1640 cell culture media supplemented with 20% fetal calf serum and 2 mM glutamine and varying concentrations of AICA riboside, and grown for 48 hours in an atmosphere of 5% carbon dioxide in air. Fetal calf serum contains purines and purine metabolizing enzymes, however, and to establish the effect of AICA riboside during 2-deoxyglucose exposure, the WI-L2 cells were incubated in RPMI 1640 medium supplemented with 10% heat-inactivated, dialyzed fetal bovine serum, 2 mM glutamine, and 1 $\mu$M deoxycoformycin.

Catabolism of cellular ATP stores was stimulated by adding either 2-deoxyglucose or a calcium ionophore. At various times, the amount of adenosine released by the cells into the supernatant, or the amount of nucleotides remaining in the cells, was determined by mixing 30 $\mu$l of chilled 4.4N perchloric acid with 300 $\mu$l of supernatants, or by adding 300 $\mu$l of chilled 0.4N perchloric acid to the cell collected as pellets and centrifuging the mixtures at 500×G for 10 minutes at 4° C. Each resulting supernatant was neutralized with 660 $\mu$l of a solution containing 2.4 grams of tri-n-octylamine (Alamine 336) (General Mills) in 12.5 ml of 1,1,2-trichloro-1,2,2-trifluoroethane (Freon-113) solvent as described by Khym in *Clinical Chemistry*, Vol. 21, p. 1245, 1975. Following centrifugation at 1500×G for three minutes at 4° C., the aqueous phase is removed and frozen at $-20°$ C. until assayed for adenosine, inosine, or for nucleotides. Adenosine was evaluated isocratically on a C-18 microBondapak reverse phase column equilibrated with 4 millimolar potassium phosphate, (pH 3.4):acetonitrile 60% in water (95:5 v/v) buffer. Adenosine elutes at 8–10 minutes, and its identity was confirmed by its sensitivity to adenosine deaminase and by spiking with adenosine standards. The extracted samples from the cell pellet were analyzed for nucleotides by high pressure liquid chromatography on a Whatman Partisil-10 (SAX) column equilibrated with 10 millimolar potassium phosphate, pH 3.78, and eluted with a linear gradient to a 0.25 molar potassium phosphate, 0.5 molar KCl, pH 3.45. Continuous monitoring was performed by absorbance at 254 and 280 nm. Peaks were quantitated by comparison with high pressure liquid chromatography analysis of suitable standards.

Figure 2:
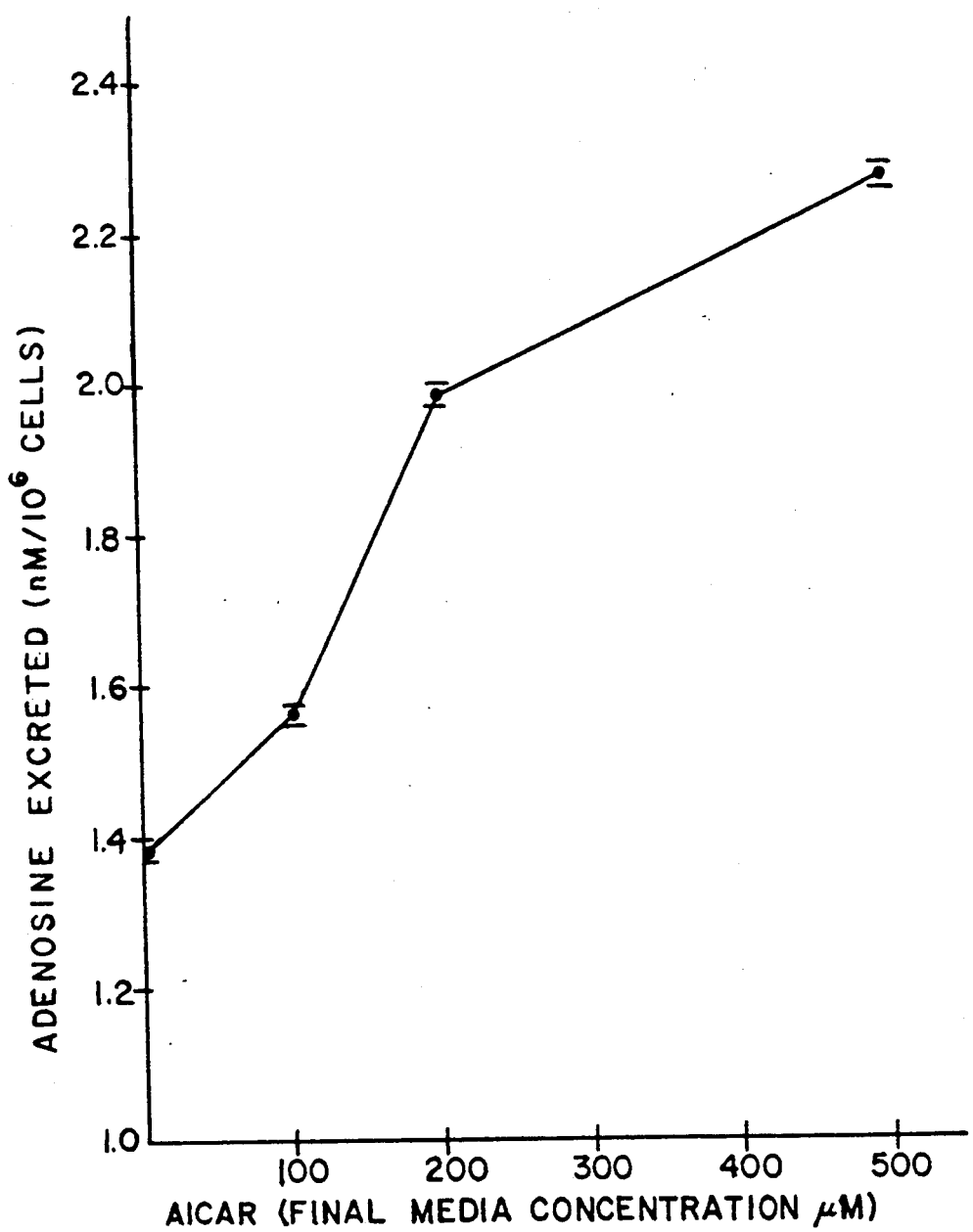
FIG. 2. In vitro effect of 48-hour preincubation with AICA riboside on adenosine excretion by human lymphoblasts during ATP breakdown.
Figure 7:
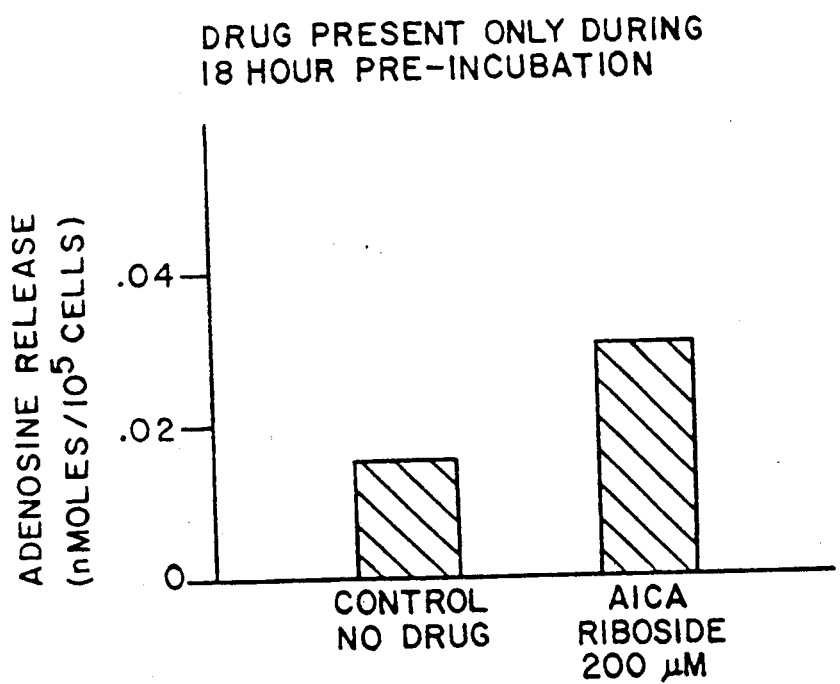
FIG. 7. Effects of 18-hour preincubation with AICA-riboside on adenosine excretion by human lymphoblasts during ATP breakdown.
Figure 8:
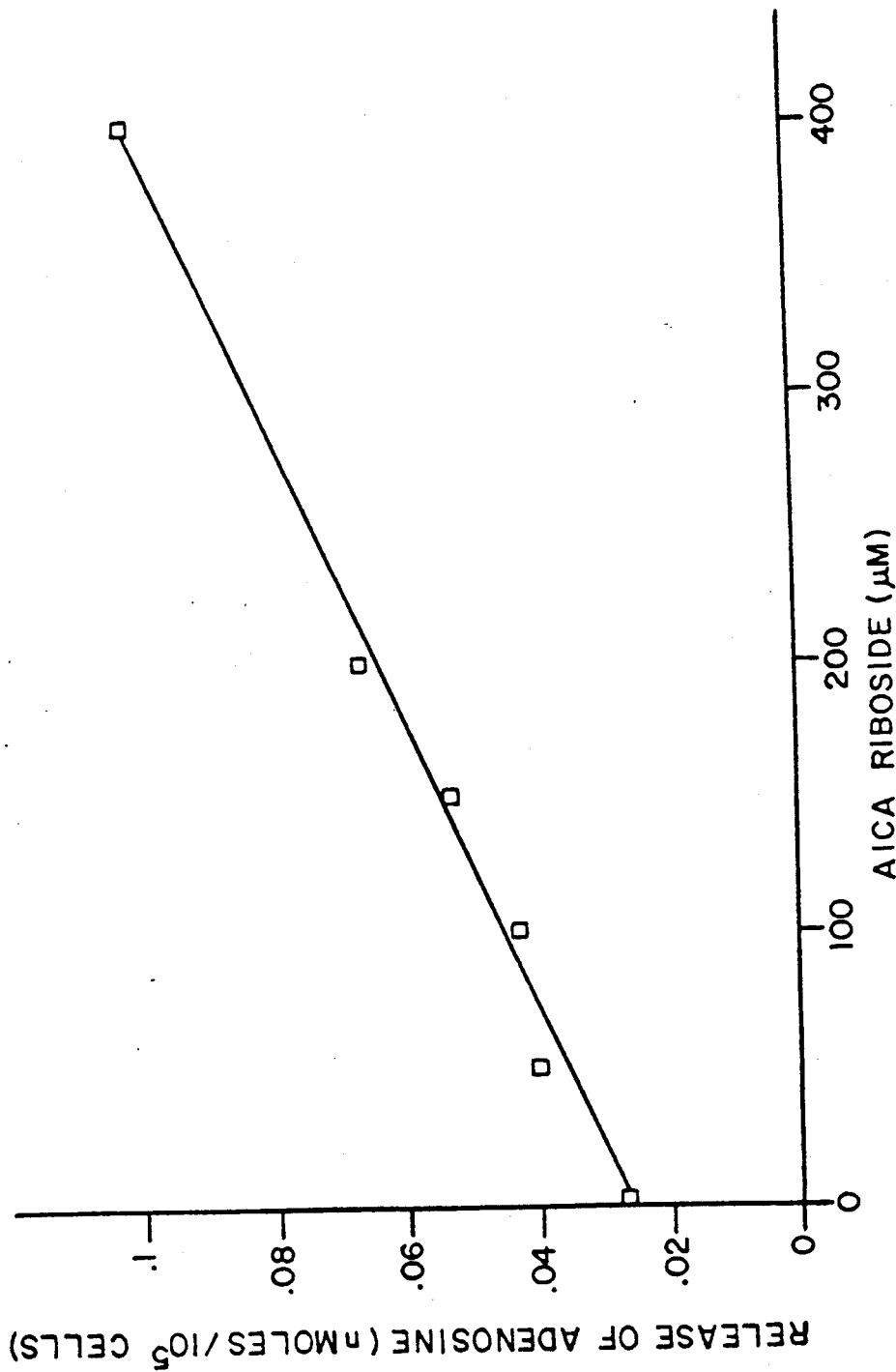
FIG. 8. Effect of three-hour preincubation and four-hour incubation with AICA riboside on in vitro adenosine excretion by human lymphoblasts during ATP breakdown.
Figure 9:
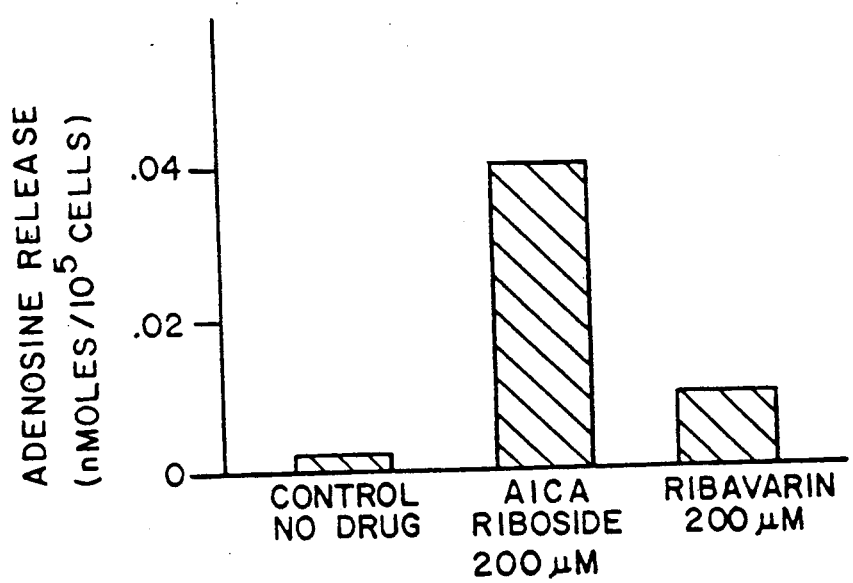
FIG. 9. Increased in vitro adenosine release from human lymphoblasts on treatment with ribavirin.

FIG. 2 shows that 48-hour AICA riboside pretreatment, over the range of 100–500 micromolar, enhances adenosine release from lymphoblasts. About 1.4 nanomoles of adenosine/$10^6$ WI-L2 cells is excreted without the presence of drugs of the invention, and this number was increased to about 2.3 nanomoles at 500 micromolar AICA riboside. When the cells are preincubated with AICA riboside for 18 hours before 2-deoxyglucose exposure, enhanced adenosine release occurs as seen in FIG. 7. Three-hour preincubation and four-hour incubation (during 2-deoxyglucose treatment) with either AICA riboside (FIG. 8) or ribivirin (FIG. 9) also results in increased adenosine release. Cells were grown to about $0.5\times 10^6$ cells/ml (mid-log phase) in FIG. 2 and to about $1.0\times 10^6$ cells/ml (early stationary phase) in FIGS. 7–9.

EXAMPLE II

In vitro effect of AICA riboside on adenosine release neuroblastoma cells

There are neuromuscular diseases such as cerebral palsy, autism, schizophrenia, and insomnia where increased adenosine release may be beneficial. Neuroblastoma cell lines were grown in media and under conditions described in Example I. Media was supplemented with 0 or 50 μM AICA riboside. To induce ATP catabolism, the growth medium was replaced by medium containing micromolar amounts of the calcium ionophore A23187 and 1.0 μM deoxycoformycin. Under these conditions it was shown that treated cells secreted at least twofold more adenosine than control cells. Cells deficient in hypoxanthine phosphoribosyl transferase secrete twofold less adenosine than cells with normal enzyme and can be corrected by pretreatment with AICA riboside or ribavirin. The results are shown in Table I below.

TABLE 1

EFFECT OF AICA RIBOSIDE ON ADENOSINE EXCRETION BY STIMUALTED HPRT− AND HPRT+ NEUROBLASTOMA CELLS

| Cell Line | Concentration of Ionophore (μg/ml) | Concentration of AICA RIBOSIDE (μM) | Concentration of Adenosine (μM) |
|---|---|---|---|
| HPRT+ | 0 | 0 | <0.01 |
| HPRT+ | 0 | 50 | <0.01 |
| HPRT− | 0 | 0 | <0.01 |
| HPRT− | 0 | 50 | <0.01 |
| HPRT+ | 10 | 0 | 0.329 |
| HPRT+ | 10 | 50 | 0.698 |
| HPRT− | 10 | 0 | 0.124 |
| HPRT− | 10 | 50 | 0.513 |

EXAMPLE III

In vivo effect of AICA riboside on adenosine levels and increased blood flow in dogs Experiments were conducted on dogs to test for increased adenosine levels caused by AICA riboside treatment, and the concomitant increase in blood flow resulting therefrom.

Figure 3:
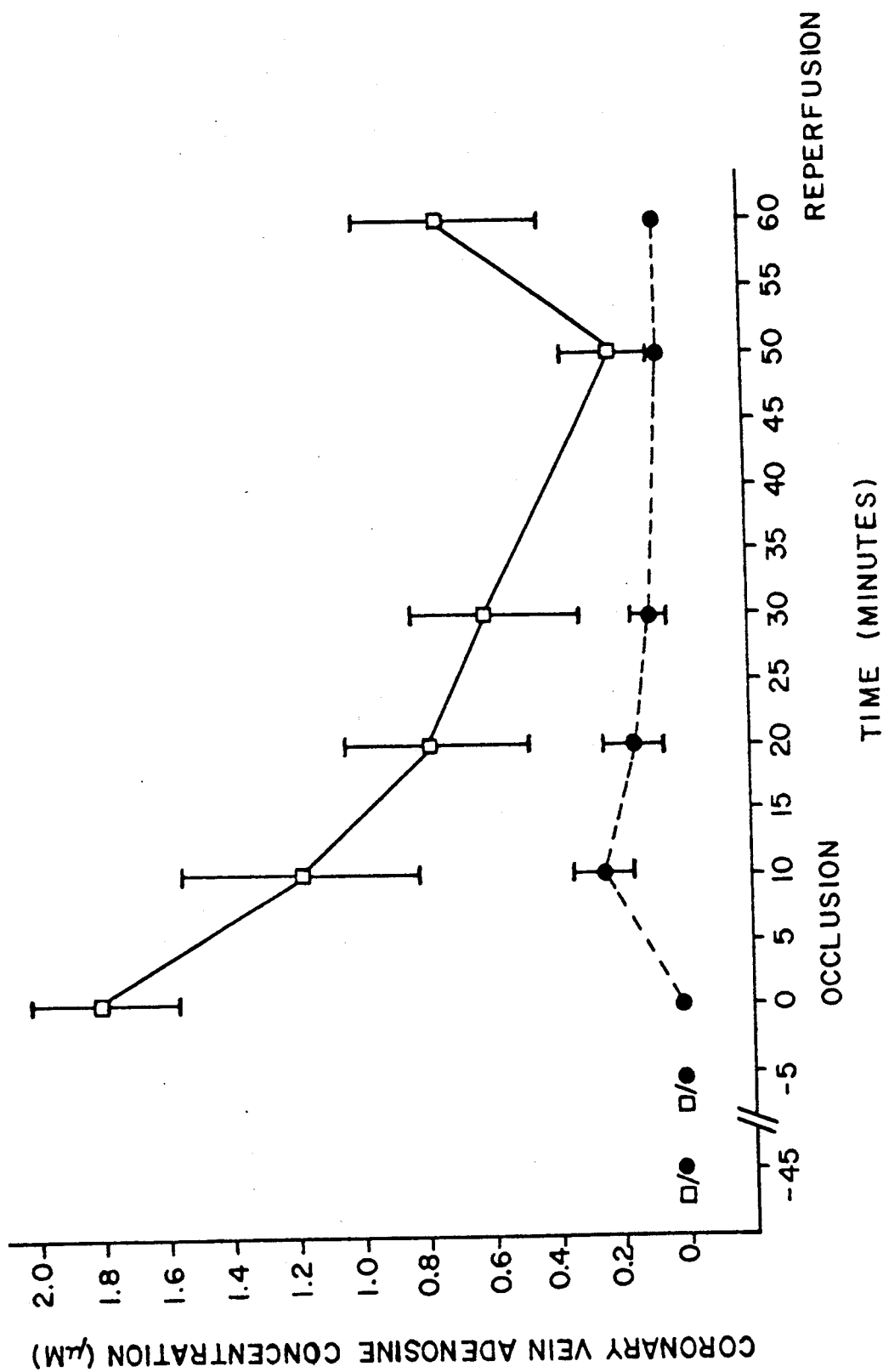
FIG. 3. The effect of AICA riboside treatment on coronary venous adenosine concentrations. Coronary venous blood was collected into chilled 2N perchloric acid at various times before and after coronary artery occlusion. Supernatants from these extracts were neutralized with alamine and freon and evaluated by high performance liquid chromotography. The mean adenosine concentrations $+/-$ standard deviations for the five saline treated (●) and six AICA riboside treated (□) dogs are graphed.
Figure 4:
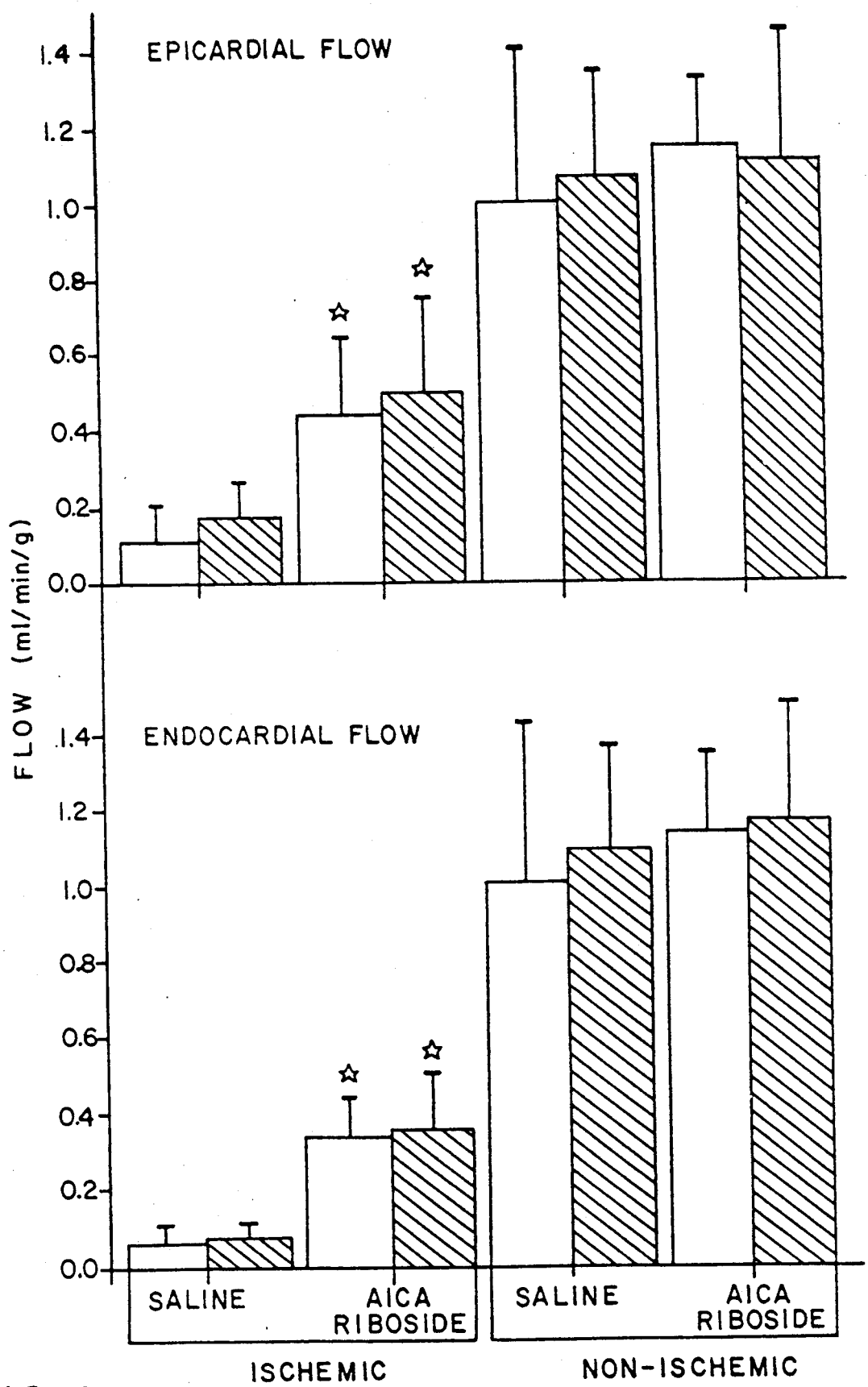
FIG. 4. In vivo effect of AICA riboside on regional myocardial blood flow during coronary artery occlusion in dogs. Regional myocardial blood flow was measured using radiolabelled microspheres infused into the left atrium at 5 minutes (open) and 60 minutes (hatched) of occlusion. The means plus the standard deviations are graphed. The asterisks (*) identify differences from saline-treated dogs that are significant at $p<0.01$.

FIGS. 3 and 4 show the results of a second series of experiments carried out to demonstrate the effects of AICA riboside on adenosine levels in blood and to correlate, the increase in adenosine with increased blood flow. Thirteen mongrel dogs were anesthetized with phenobarbital. The anterior coronary vein was cannulated and a blood sample was collected into 2N perchloric acid. Saline or 100 mM AICA riboside in saline was randomly selected for infusion into the femoral vein for 45 minutes prior to coronary artery occlusion at a rate of 1 ml/min. Coronary venous blood was collected and assayed for adenosine in a manner similar to the assay described in Example I at 5 minutes prior to occlusion, and after 1, 10, 20, 30 and 50 minutes of occlusion of the left anterior descending coronary artery, as well as 1 minute after reperfusion. Regional myocardial blood flow was measured within 15 μm radiolabelled spheres infused into the left atrium at 5 and 60 minutes during the ischemic period, as described by Heymann et al. in Prog. C.V. Dis. 20; 55 (1977). The electrocardiogram and arterial pressure were monitored throughout the period of ischemia. Six AICA riboside-treated and five saline-treated dogs survived the procedure. Two of the surviving saline-treated animals fibrillated. The concentration of AICA riboside in AICA riboside-treated dogs immediately before occlusion was 57.4+/−40.2 μM. The range was 4.4 to 100 μM.

FIG. 3 shows that adenosine levels in blood draining ischemic areas are dramatically increased in AICA riboside perfused dogs. Prior to ischemia, none of the dogs had measurable venous adenosine (<0.01 μM) before and during AICA riboside or saline infusion. The saline-treated animals had a peak adenosine level at 10 minutes after occlusion (0.22+/−0.08 μM) which fell to an undetectable level by 60 minutes. In contrast, the AICA riboside-treated animals had a peak adenosine level at 1 minute of ischemia (1.79+/−0.35 μM) which remained elevated at 60 minutes (0.18+/−0.15). Reperfusion resulted in no detectable adenosine washout in saline-treated animals but a significant rise in the AICA riboside-treated animals. Blood obtained from the right atrium (sampling of systemic blood) had no detectable adenosine in saline—and AICA riboside-treated dogs.

FIG. 4 shows that regional myocardial blood flow to the ischemic myocardium was significantly greater in AICA riboside than in saline-treated animals. A similar degree of difference in flow was seen in endocardium and epicardium, and there were no changes between 5 and 60 minutes of ischemia. AICA riboside did not alter flow to normal myocardium, as the non-ischemic tissue flow rates are remarkably similar between the two groups. Systemic arterial pressure and heart rate at 5 and 60 minutes showed no significant differences between the two groups of dogs. Arterial blood gas-content and systemic venous granulocyte counts were not significantly different between the two groups. Thus, AICA riboside is believed to enhance collateral coronary flow to ischemic myocardium, as indicated above, by augmenting localized adenosine release and thus vasodilating vessels in the ischemic region and/or inhibiting granulocyte free radial production and subsequent capillary damage and/or plugging.

EXAMPLE IV

Effect of AICA riboside treatment on inosine levels in dogs

Figure 5:
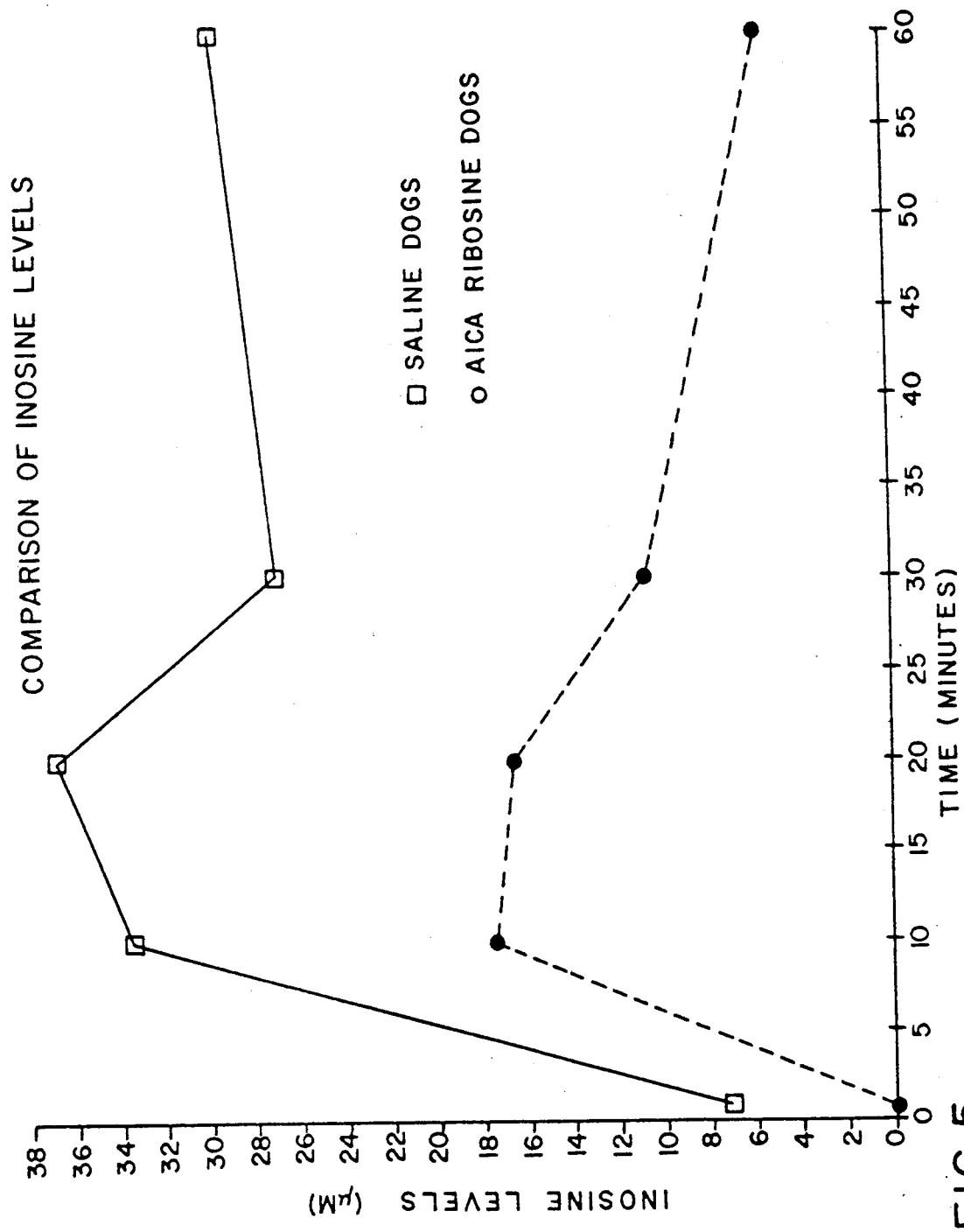
FIG. 5. Comparison of the effects of AICA riboside treatment (●) and control treatment containing only saline (□) on inosine levels in dogs.

That the increase in the levels of adenosine is due, at least in part, to a reduction in the amount of ATP that is converted to inosine was shown by analysis of venous blood from dogs in Example III for inosine levels. FIG. 5 shows a more than twofold decrease in inosine levels over the 60-minute assay period in AICA riboside-treated dogs. These data indicate that the compounds of the invention increase adenosine release by redirecting the catabolism of ATP from the normally more prevalent end product, inosine, to adenosine.

EXAMPLE V

Effect of AICA riboside treatment on myocardial infarct size

The effect of AICA riboside treatment on myocardial infarct size was determined in rats given a bolus of either AICA riboside in saline or saline alone, and then inducing restricted blood flow by tying off the left anterior descending coronary artery. The animals were continuously exposed by infusion of either AICA riboside in saline or saline using osmotic mini-pumps well known to those in the art. After three weeks, the rats were sacrificed and infarct size quantitated by planimarizing stained sections of fixed hearts. The results showed that in AICA riboside treated hearts there is a reduction of infarct size of 33% compared to saline-treated controls (p<0.05).

EXAMPLE VI

Effect of AICA riboside treatment on arrhythmias

One consequence of myocardial ischemia is arrhythmia and the frequency of arrhythmias is related to the degree of reduced blood flow. Because adenosine is known to act as an anti-arrhythmic and to supress granulocyte free radical production, which can cause arrhythmia through lipid peroxidation, the prophylactic effect of AICA riboside treatment on arrhythmias was determined. Electrocardiograms recorded during ischemia of Example III were analyzed for the number of premature ventricular depolarizations (PVD) and ventricular tachycardia (VTAC) episodes. Table 2 shows that the saline—treated dogs had 112.2 PVD and 18.2 episodes of VTAC during ischemia, as compared to 37.8 PVD and 4.7 episodes of VTAC for the AICA riboside treated animals ($p<0.01$). The one AICA riboside-treated dog (#3) with frequent arrhythmias had much lower collateral blood flow rates and adenosine concentrations (but an AICA riboside blood concentration of 27.2 $\mu$M) compared to the other AICA riboside-treated dogs.

| TREATMENT GROUP | ARRHYTHMIAS (EPISODES/H) | |
|---|---|---|
| | PVD | VTAC |
| SALINE | | |
| 1 | 101 | 10 |
| 2 | 144 | 23 |
| 3 | 232 | 44 |
| 4 | 57 | 8 |
| 5 | 27 | 6 |
| AVERAGE | 112.2 | 18.2 |
| AICA RIBOSIDE | | |
| 1 | 12 | 1 |
| 2 | 10 | 0 |
| 3 | 182 | 27 |
| 4 | 4 | 0 |
| 5 | 13 | 0 |
| 6 | 6 | 0 |
| AVERAGE | 37.8 | 4.7 |

EXAMPLE VII

Inhibition of AMP Deaminase by AICA ribotide and related molecules

As shown in the experimental results set forth in FIG. 6, the AMP-utilizing enzyme, AMP deaminase, is inhibited by the phosphorylated derivatives of AICA riboside and ribavirin. The phosphorylated forms are referred to as AICA ribotide and ribavirin monophosphate, respectively. Using 200 $\mu$M of each ribotide, AMP deaminase was inhibited 38% and 54%, respectively. The enzyme assay is performed by measuring the conversion of $^{14}$C-AMP to $^{14}$C-IMP (adapted from T. J. Wheeler and J. M. Lowerstein, *J. Biol. Chem.* 254:8994 (1979). The reaction is performed using cytoplasmic lysates from a human lymphoblast line as described by Gruber et al., *Biochim. Biophys. Acta* 846:135-144, 1985. The substrates and products are separated on thin layer chromatography plates and counted in a liquid scintillation counter. Inhibition of this enzyme leads to an increase in the concentration of AMP, the direct precursor to adenosine; in the cell.

EXAMPLE VIII

Effect of Adenosine on Granulocyte/Endothelial Cell Interaction

Studies were undertaken to demonstrate whether adenosine reduces the adhesive affinity, or "stickiness" of granulocytes for endothelial cells, an event which should increase blood flow in microvessels. The parameter measured was the fracture stress between the two cell types.

Adenosine decreases fracture stress between granulocytes and endothelial cells (which line the walls of vessels) by a factor of two as measured by a twofold increase in the rolling velocity of granulocytes in microvessels exposed to adenosine by superfusion with a solution of 20 $\mu$M, yielding a concentration of approximately 2 $\mu$M in the vessel. These studies were performed by intravital microscopy filming of granulocytes in rat mesentary microvessels. The rolling velocity of granulocytes compared to the streaming velocity of red cells was calculated before and after the administration of adenosine.

EXAMPLE IX

Effect of AICA Riboside on Granulocyte Accumulation in Ischemic Myocardium

AICA riboside decreases the accumulation of $^{111}$indium-labelled granulocytes in ischemic myocardium. In a series of dogs as described in Example III, granulocytes were removed and labelled with $^{111}$indium and re-infused. After one hour of ischemia, the animals were sacrificed and, the granulocytes quantitated in myocardial tissue by determining $^{111}$indium content in myocardial biopsies using a gamma counter. Granulocyte content in the ischemic endocardium was significantly less in AICA riboside-treated dogs ($1.03+/-0.21\times10^6$ cells/gram) than in saline-treated animals ($1.55+/-0.24\times10^6$ cells/gram). Radiolabelled microsphere determination of collateral blood flow yielded essentially identical results to those shown in Example III, i.e., blood flow in the AICA riboside-treated dogs was significantly greater than in saline-treated animals.

EXAMPLE X

Treatment of Autistic Patients with AICA Riboside

Studies were conducted to determine the beneficial effects of treating autistic individuals with AICA riboside.

Following authorization, therapeutic trials with AICA riboside were started in two patients with adenylosuccinase deficiency (autism). The therapeutic trial was initiated on Day 1 by the oral administration of AICA riboside at the single dose of 5 mg/kg/day. That same day, blood and urine samples were collected at various time intervals and a single lumbar puncture was performed on each patient, respectively, two and three hours after the administration of AICA riboside. In view of the absence of clinical side effects, the same dose of AICA riboside was given during the following days, during which the patients remained in the hospital, and urine collection was continued. Since no adverse effects of the administration of the nucleoside were noticed, the dosage of AICA riboside was increased to 2×5 mg/kg/day and the patients discharged on Day 8, with this therapy. On Day 55, both patients were briefly readmitted for clinical, biochemical and psychiatric evaluation. In the absence of any clinical side effects, the dosage of AICA riboside was increased to 2×10 mg/kg/day from Day 46, on. Treatment was maintained until Day 71, and arrested at that date.

On Day 119 an intravenous loading test was performed with a dose of 20 mg/kg/day, followed after one hour by a lumbar puncture, with the particular purpose of assessing the penetration of AICA riboside in the cerebro-spinal fluid (CSF).

At all dosages used, AICA riboside could not be detected in plasma and CSF with available methodology. The nucleoside is nevertheless reabsorbed in the gut, as evidenced by the finding that during chronic oral administration its triphosphate derivative, AICA riboside triphosphate, was present in the erythrocytes. One hour after intravenous administration, AICA riboside was also undetectable in plasma, but AICA riboside triphosphate had similarly accumulated in the erythrocytes, indicating a rapid cellular uptake and metabolism of AICA riboside. A correct assessment of the renal loss of the nucleoside could not be obtained.

The administration of AICA riboside remained without significant effect on the urinary output of the two abnormal compounds excreted by these patients, succinyladenosine and SAICA riboside, and on that of uric acid. It also did not influence significantly the concentration of ATP and GTP in the erythrocytes. The concentrations of AICA riboside triphosphate reached, following oral as well as intravenous administration of AICA riboside, were of the same magnitude as those of GTP.

Appraisal of the mental development of both patients just prior to the initiation of the therapeutic trial with AICA riboside showed profound psychomotor retardation (mental development around three months on Bayley scales), accompanied by the following autistic features: stereotypic incoordinate movements, absence of reaction to auditory and tactile stimuli, and poor reaction to visual stimuli.

Reassessment of these features, after two months of continuous AICA riboside administration did not show any modification in the older patient. His younger sister, however, displayed a clear-cut improvement: stereotypic movements were less frequent, response to visual stimuli was improved and, most noteworthy, reactions to auditory and tactile stimuli could now be recorded. Two months later, following the six-week interruption of AICA riboside treatment, both patients were described as "more pleasantly active and more easy to handle during therapy" by the father, thereby prompting his request for resumption of the trial.

The following parameters were found normal before and during the trial treatment with AICA riboside: red blood cell count, white blood cell count, platelet and reticulocyte counts; leukocyte differentiations; hematocrit, ionogram, Ca, P, urea, creatinine, uric acid, cholesterol, lipids, SGOT, SGPT, CPK, glucose, lactate and ammonia.

EXAMPLE XI

Effect of Ribavirin on Mast Cell Degranulation

By preventing mast cell degranulation, it is possible to prevent or control a patient's allergic response. Bone marrow obtained from Balb/C mice femurs was cultured in a 1:1 mixture of Razin media and conditioned media, produced by co-culturing splenocytes from C57B1/6J and C3H mice in the present of Concanavalin A as described by Razin et al. in the *Proc. Natl. Acad. Sci. U.S.A.* 28: 2559–2561, 1981. After weekly passaging and at least 15 days in tissue culture, the resulting cells were 90% pure mast cells and 95% viable as assessed by Trypan blue exclusion. Cells exposed to ribavirin in culture were washed three times prior to use in experiments. Parallel cultures of cells grown in media alone were used as controls for pharmacologically manipulated mast cells. Cell growth was assessed by counting cells at particular time points and comparing actual numbers of ribavirin-treated cells to numbers of cells grown in media alone.

$\beta$-hexosaminidase was chosen as a representative granule-associated, preformed mast cell mediator because it is easily quantitated, and its release nearly identically parallels that of histamine. Mouse bone marrow-derived mast cells were centrifuged at $200 \times$ g for 5 minutes, washed three times in Tyrode's buffer lacking divalent cations, sensitized for 30 minutes at 37° C. with anti-DNP (dinitrophenyl phosphate) IgE (1 $\mu g/10^6$ cells), and challenged with either DNP-BSA antigen (175 ng/$3 \times 10^5$ cells) or A23187 (10 $\mu g/ml/3 \times 10^5$ cells) in 400 $\mu l$ of complete Tyrode's buffer for 10 minutes at 37° C. Reaction mixtures were centrifuged at $200 \times$ g for 10 minutes, and supernatant and pellet $\beta$-hexosaminidase concentrations were assayed by the hydrolysis of p-nitrophenyl-$\beta$-D-glucosamide as described in Schwartz et al. in *J. Immunol.* 123, 1445 (1979). Spontaneous $\beta$-hexosaminidase release was determined in unchallenged cells. The net % of $\beta$-hexosaminidase released is defined as follows:

$$\text{Net \% } \beta\text{-hex released} = \frac{\text{super. }[\beta\text{-hex}]}{\text{super. }[\beta\text{-hex}] + \text{pellet }[\beta\text{-hex}]} - \text{spontaneous release}$$

where [$\beta$-hex] is $\beta$-hexosaminidase and super. is supernatant. When exogenous adenosine was present in reaction mixtures, it was added simultaneously with the secretagogue.

Figure 11:
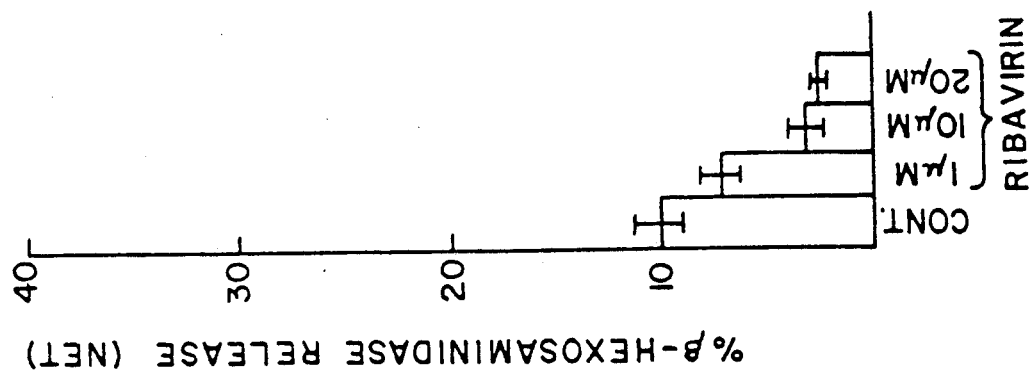
FIG. 11. Dose-response effects of ribavirin on mast cell β-hexosaminidase release. Mast cells were cultured in media alone (controls) or 1, 10, or 20 μM ribavirin for six days, washed, challenged with A23187, and net β-hexosaminidase release was quantitated. Ribavirin-treated cells at all concentrations tested released significantly less β-hexosaminidase when challenged with A23187. Mediator content and spontaneous release were no different in control and ribavirin-exposed cells. Depicted are means +/− SE of duplicate determination from three experiments.
Figure 10:
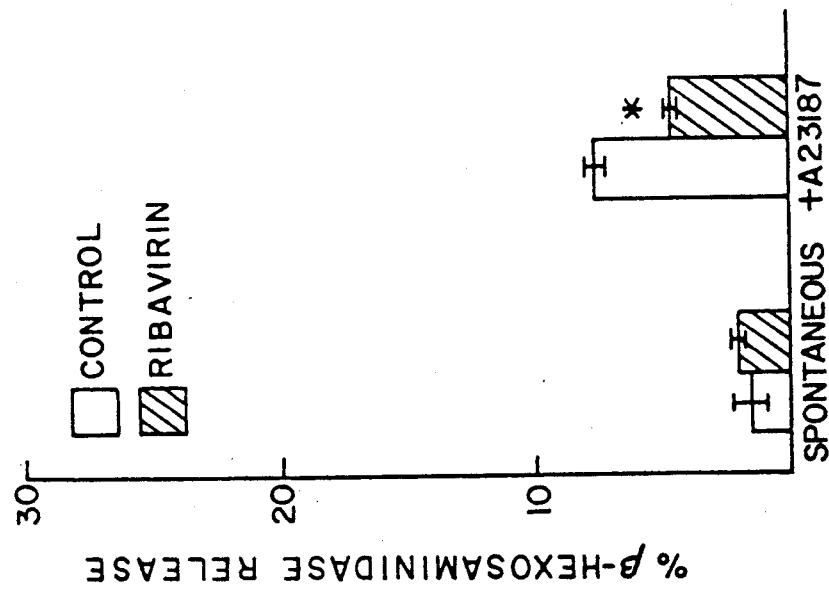
FIG. 10. $\beta$-hexosaminidase release from control and ribavirin-treated mast cells. Mouse bone marrow-derived mast cells cultured for three to seven days in media alone (open) or 10M ribavirin (hatched) were challenged with the calcium ionophore A23187. The percentages of β-hexosaminidase release from resting and stimulated cells are shown as means +/− SE of duplicate values from seven experiments. The asterisks (*) identify data significantly different from control cells ($p<0.05$). Similar results were obtained with DNP-BSA antigen stimulation of anti-DNP IgE-sensitized mast cells.

Mouse bone marrow-derived mast cells challenged with A23187 or DNP-BSA antigen released 8–15% of total cell $\beta$-hexosaminidase, a preformed, granule-associated mediator. Ribavirin (10 $\mu M$) added at the time of mast cell stimulation does not affect $\beta$-hexosaminidase release. However, mast cells incubated for three to seven days in 10 $\mu M$ ribavirin, washed, and challenged with A23187 exhibited a marked attenuation of $\beta$-hexosaminidase release compared to parallel cells cultured in media alone (FIG. 10). The asterisks (*) identify data significantly different from control cells (p<0.05). Ribavirin exposure did not alter mast cell mediator content (i.e., total cell $\beta$-hexosaminidase concentration) nor cell viability, and spontaneous release of $\beta$-hexosaminidase was similar in the two cell groups. The dose-response relationship between ribavirin exposure and preformed mediator release is depicted in FIG. 11. Although 1 $\mu M$ ribavirin for six days inhibits mediator release significantly, maximal inhibition is evidence between 10 $\mu M$ and 20 $\mu M$.

EXAMPLE XII

Regulation of mast cell activation and degranulation by AICA riboside

The activation and degranulation of mast cells play a key role in allergic diseases such as asthma. Thus, a means of preventing activation and degranulation affords a way to control the disease.

A. Mast cell isolation

To demonstrate the prevention of degranulation and activation by the claimed method, the cells were first isolated and cultured as described in Example XI.

B. Effect of AICA riboside on degranulation

Inhibition of degranulation by AICA riboside was demonstrated by showing that AICA riboside inhibits degranulation induced by the calcium ionophore, A23187, as reflected in the release of the acid exoglycosidase, $\beta$-hexosaminidase. A23187 at 1 $\mu$g/ml, with or without AICA riboside, was added to $2-5 \times 10^6$ mast cells at 37° C. on Tyrode's buffer, and the amount of mast cell $\beta$-hexosaminidase released measured. In the presence of 100 micromolar AICA riboside, only 17.6% of $\beta$-hexosaminidase was released, whereas 28.8% was released in its absence. Thus AICA riboside inhibits mast cell degranulation. The percent release of $\beta$-hexosaminidase, as well as the method of assaying for the enzyme, was performed as described by Schwartz et al. in the *J. of Immun.*, Vol. 123, October, 1979, p. 1445.

Effect of AICA riboside on leukotriene $C_4$ release

Cells grown in medium alone or with 100 $\mu$M AICA riboside for six days were washed and challenged for 20 minutes with A23187. Supernatant leukotriene $C_4$ concentrations were determined by radioimmune assay and demonstrated to be 51 and 13 nanograms/$10^6$ cells for control and AICA riboside-treated cells, respectively. Leukotriene $C_4$ release was significantly reduced ($p<0.01$) by 75% with AICA riboside pretreatment. Similar results were obtained on four- to six-day pretreatment with 10 $\mu$M ribavirin where mast cell activation was accomplished with antigen binding to IgE on the mast cell surface.

EXAMPLE XIII

Suppression of Pentylene Tetrazol-Induced Seizures

To test the ability of AICA riboside to suppress pentylene tetrazol-induced seizures, rats (10 for each condition) were pretreated (randomly and blinded) with intraperitoneal AICA riboside in saline (0.9%) at 1000 mg/kg or 100 mg/kg, or an equal volume of saline for 30 minutes and 5 minutes before injection of 60 mg/kg pentylene tetrazol. The animals were observed for one hour by two independent seizure experts.

There was a 40% reduction of animals having seizures in the group that received 2000 mg/kg (total dose) and a dramatic prolongation of latency to seizure in this group (FIG. 12).

EXAMPLE XIV

Suppression of Catecholamine-induced Arrhythmia

To determine whether AICA riboside would protect the heart from isoproterenol (isuprel)-induced arrhythmias, nine pairs of rats were tested with one animal of each pair injected intraperitoneally with 1000 mg/kg of AICA riboside in water. The other animal of each pair served as a control and was similarly injected with saline (0.9%) in a volume equal to that of the AICA riboside solution.

Five minutes later both animals were anesthetized with 330 mg/kg of chloral hydrate injected intraperitoneally. Then a single EKG lead was attached to each rat for simultaneous recording of the paired rats' electrocardiograms. To produce arrhythmia, each rat was injected subcutaneously with isuprel (1000 mg/kg).

Beginning 30 minutes after isuprel introduction, the electrocardiograph recording paper speed was run (5 cm/sec) for 10 minutes to count the arrhythmic beats of both animals.

Figure 13:
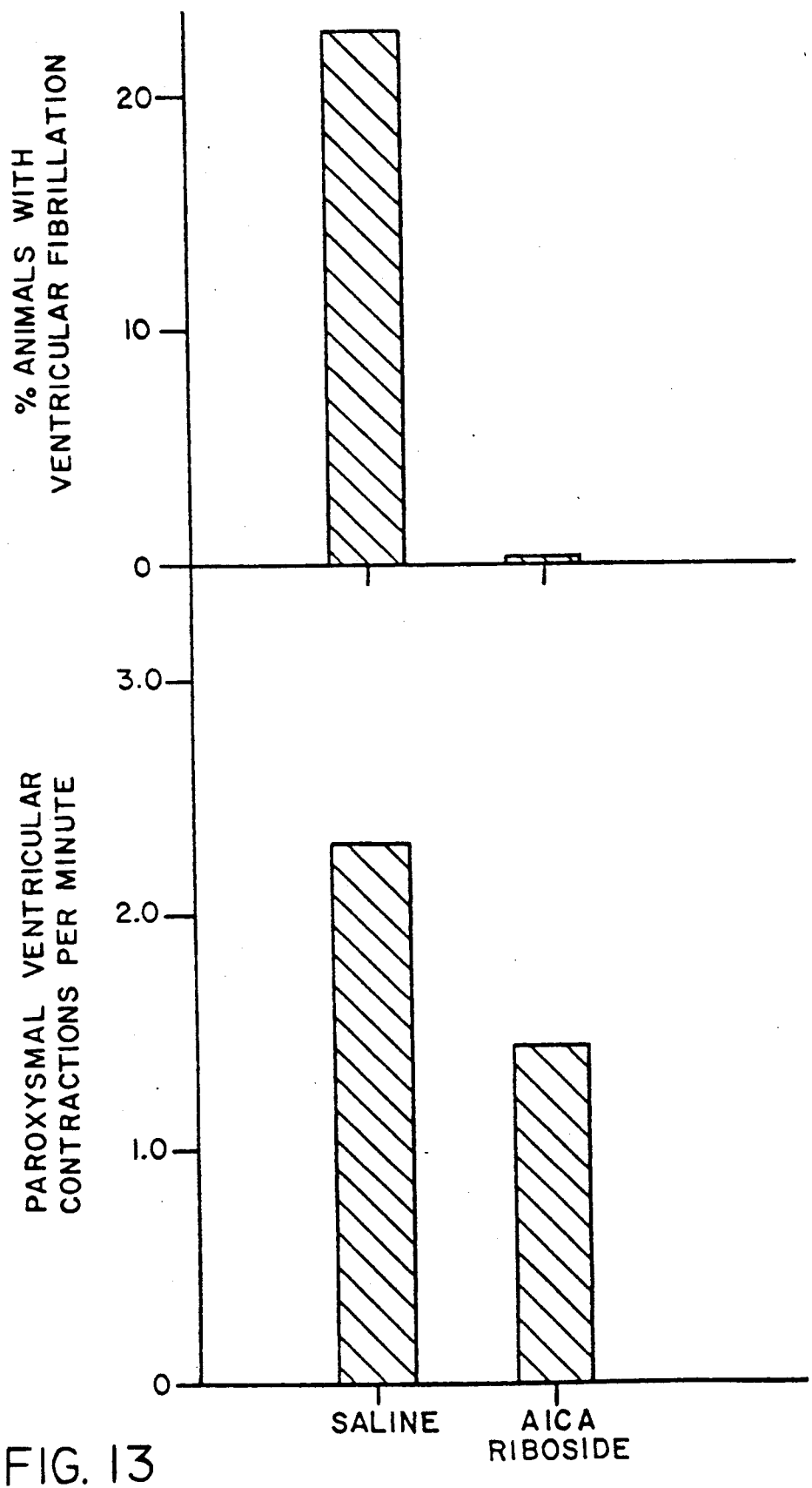
FIG. 13. AICA riboside inhibition of isuprel-induced arrhythmias in the rat.

There was a 39% reduction in paroxysmal ventricular contractions and a complete suppression of ventricular fibrillation in the AICA riboside-treated rats (FIG. 13).

It will be evident that there are many embodiments of the present invention in both its method and composition aspects which are not described above but which are clearly within the scope and spirit of the invention. The above description is therefore intented to be exemplary only, and the scope of the invention is to be defined solely by the appended claims.

I claim:

1. A method for decreasing or preventing mast cell activation in a patient comprising the administration of a therapeutically effective amount of a purine nucleoside compound or analog which inhibits mast cell degranulation or production of leukotrienes or both.

2. The method of claim 1 wherein said purine nucleoside compound or analog is selected from the group consisting of AICA riboside, AICA ribotide, ribavirin, and ribavirin monophosphate.

3. A method for treating allergic conditions in a patient comprising the administration to said patient of a therapeutically effective amount of a compound selected from the group consisting of AICA riboside, AICA ribotide, ribavirin, and ribavirin monophosphate.

4. The method of claim 3 wherein said allergic condition is hay fever.

5. The method of claim 3 wherein said allergic condition is asthma.

6. The method of claim 3 wherein said allergic condition is eczema.

7. The method of claim 3 wherein said allergic condition is chronic urticaria.

8. The method of claim 3 wherein said allergic condition is urticaria pigmentosa.

9. The method of claim 3 wherein said allergic condition is allergic conjunctivitis.

10. The method of claim 3 wherein said allergic condition is allergic rhinitis.

11. A method of treating an animal body for allergy comprising administering to said animal body a therapeutically effective amount of the purine nucleoside 5-amino-1-($\beta$-D-ribofuranosyl)-imidazole-4-carboxamide.

12. A method as described in claim 11 wherein said 5-amino-1-($\beta$-D-ribofuranosyl)-imidazole-4-carboxamide is administered at concentrations up to 0.5 molar.

13. A method as described in claim 12 wherein said allergies are selected from the group consisting of hay fever, asthma, chronic urticaria, urticaria pigmentosa and eczema.

14. A method of treating an animal body for allergy comprising administering to said animal body a therapeutically effective amount of the purine nucleoside 1-$\beta$-ribofuranosyl-1,2,4-triazole-3-carboxamide.

15. A method as described in claim 14 wherein said 1-$\beta$-ribofuranosyl-1,2,4-triazole-3-carboxamide is administered at concentrations up to 0.5 molar.

16. A method as described in claim 15 wherein said allergies are selected from the group consisting of hay fever, asthma, chronic urticaria, urticaria pigmentosa and eczema.

* * * * *